(12) United States Patent
Korenev

(10) Patent No.: US 7,059,269 B2
(45) Date of Patent: Jun. 13, 2006

(54) PULSED ELECTRIC FIELD SYSTEM FOR DECONTAMINATION OF BIOLOGICAL AGENTS ON A DIELECTRIC SHEET MATERIAL

(75) Inventor: Sergey A. Korenev, Mundelein, IL (US)

(73) Assignee: Steris, Inc., Temecula, CA (US)

( * ) Notice: Subject to any disclaimer, the term of this patent is extended or adjusted under 35 U.S.C. 154(b) by 393 days.

(21) Appl. No.: 10/367,243

(22) Filed: Feb. 13, 2003

(65) Prior Publication Data

US 2004/0159540 A1 Aug. 19, 2004

(51) Int. Cl.
*C23C 16/00* (2006.01)

(52) U.S. Cl. .............................. 118/723 E; 156/345.47; 156/345.2; 156/345.24; 118/718; 118/712

(58) Field of Classification Search ............. 118/723 E, 118/718, 719, 663, 712; 156/345.43, 345.44, 156/345.45, 345.46, 345.47, 345.24, 345.25; 315/111.21
See application file for complete search history.

(56) References Cited

U.S. PATENT DOCUMENTS

| | | | | |
|---|---|---|---|---|
| 4,842,683 A | * | 6/1989 | Cheng et al. | 156/345.37 |
| 5,968,377 A | * | 10/1999 | Yuasa et al. | 219/121.41 |
| 6,007,673 A | * | 12/1999 | Kugo et al. | 156/345.1 |
| 6,181,068 B1 | * | 1/2001 | Hur et al. | 315/111.21 |
| 6,459,089 B1 | | 10/2002 | Masefield et al. | 250/453.11 |
| 6,558,889 B1 | * | 5/2003 | Oishi et al. | 430/532 |
| 6,773,736 B1 | * | 8/2004 | De Winter et al. | 426/244 |

FOREIGN PATENT DOCUMENTS

JP        2000208296 A   *   7/2000

OTHER PUBLICATIONS

Karl H. Schoenbach, Sunao Katsuki, Robert H. Stark, E. Stephen Buescher, and Stephen J. Beebe, Bioelectrics–New Applications for Pulsed Power Technology, IEEE Transaction on Plasma Science, vol. 30, No. 1, Feb. 2002, p. 293–300.

Korenev S.A. and Rubin N.B., Forming of the Bywalled Plasma in Vacuum Prolonged Channels, No. 9–82–13, Joint Institute for Nuclear Research, Dubna, 1982, pp. 1–7.

Korenev S.A., Investigation of Plasma Diode in the External Magnetic Field, No. 9–81–703, Joint Institute for Nuclear Research, Dubna, 1981, pp. 1–4.

Ivan B. Enchevich and Sergei A. Korenev, Ion Source of Discharge Type, XIII International Conference on Cyclotrons and Their Applications, Cyclotrons '92, Vancouver, Jul. 1992, pp. 1–2.

Korenev S.A. and Rubin N.B., Formation of Plasma Heat a Wall in Long Vacuum Channels, Soviet Physics Technical Physics, Oct. 1983, pp. 1187–1189.

U.S. Appl. No. 10/090,573, filed Mar. 4, 2002, Korenev, entitled: Mobile Radiant Energy Sterilizer.

U.S. Appl. No. 10/095,869, filed Mar. 12, 2002, Korenev et al., entitled: Method and Apparatus for Destroying Microbial Contamination of Mail.

(Continued)

*Primary Examiner*—Parviz Hassanzadeh
*Assistant Examiner*—Michelle Crowell
(74) *Attorney, Agent, or Firm*—Kusner & Jaffe; Michael A. Centanni

(57) ABSTRACT

A pulsed electric field system for inactivation of biological agents on a dielectric sheet material. The pulsed electric field (PEF) system includes a dielectric layer located between an active electrode and a ground electrode, wherein said dielectric layer has a uniform surface profile. A pulsed electric field is provided in a gap between the dielectric layer and the active electrode. A transport assembly moves the dielectric sheet material through the gap. In a preferred embodiment, the system also includes sensors for sensing the position of the dielectric sheet material as it passes through the pulsed electric field.

5 Claims, 4 Drawing Sheets

OTHER PUBLICATIONS

Figure 1:
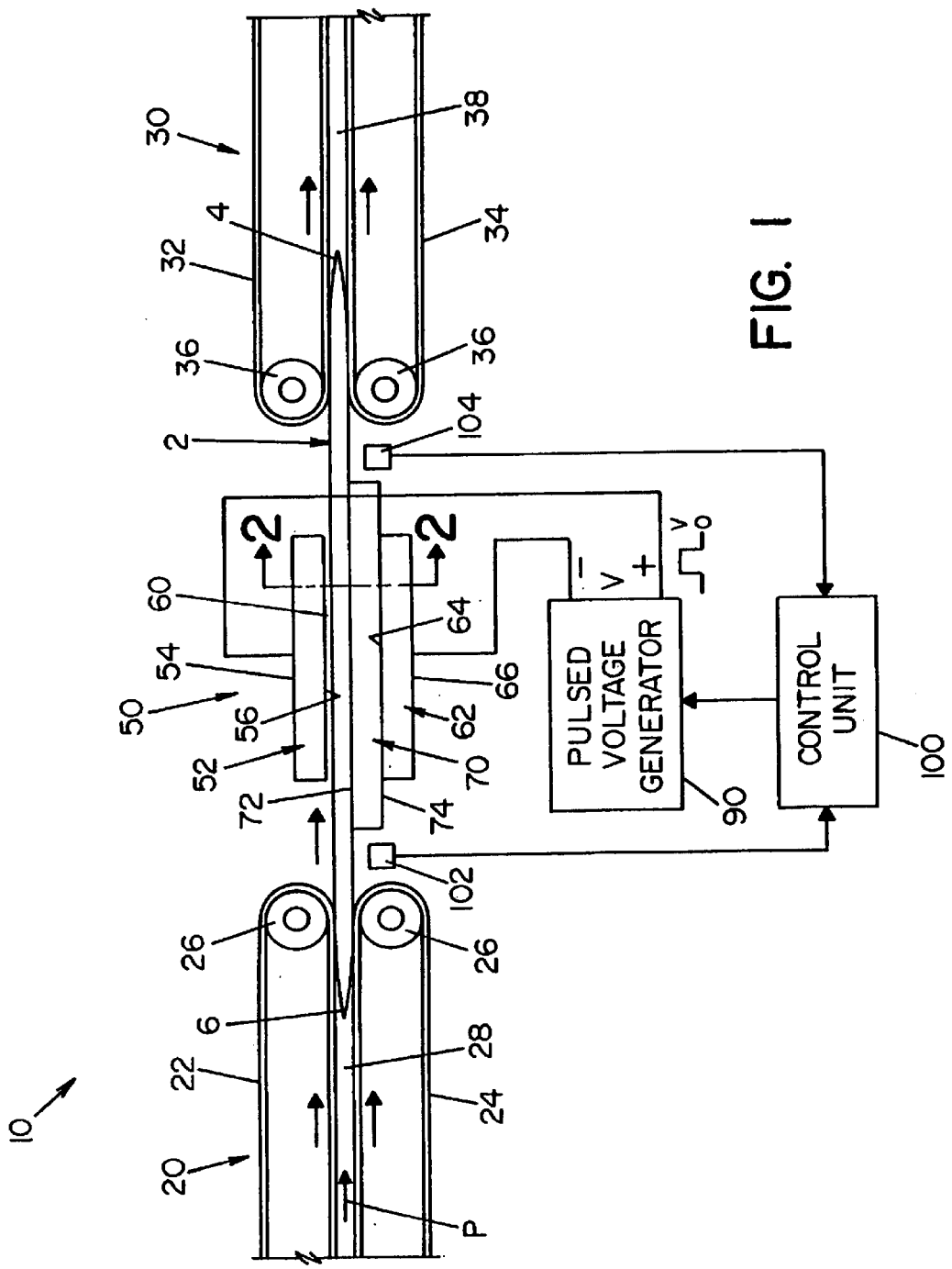

U.S. Appl. No. 10/280,950, filed Oct. 25, 2002, Mielnik et al., entitled: Decontamination of Critical Mail.

Frank et al., article entitled: "*Pseudospark Discharge Physics,*" Pulsed Technologies Ltd., 2002, 2 pages.

Mamaev et al., article entitled: "*150 kV Magnetic Pulse Compressor,*" Moscow Radiotechnical Institute of Russian Academy of Sciences, IEEE 1998, pp. 1311–1312.

Gordeev et al., article entitled: "*Design of Straus–R Accelerator,*" Russian Federal Nuclear Center–All–Russia Scientific Research Institute of Experimental Physics, Russia, BOIIBOz701z701POCbz702 ATOMHOz703 HAz704 z705 TEXHz706, 2001, No. 3, pp. 56–58.

Article entitled: "*Kinetics of Microbial Inactivation for Alternative Food Processing Technologies Pulsed Electric Fields,*" U.S. Food and Drug Administration, Center for Food Safety and Applied Nutrition, Jun. 2, 2000, pp. 1–37.

Barbosa–Cáovas et al., article entitled: "*Pulsed Electric Power in Food Preservation,*" Biological Systems Engineering, Washington State University.

George et al., article entitled: "*Making Submicron Features by Ion Etching Through PMMA Masks,*" NASA's Jet Propulsion Laboratory, pp. 1–2, Oct. 2000.

Kondratenkov et al., article entitled: "*Superpower Semiconductor Switch Based on Reversed Switched Dinistor,*" ISTC Project 0907.

Article entitled: "*Hydrogen Thyratrons Preamble,*" Marconi Applied Technologies Limited.

\* cited by examiner

PULSED ELECTRIC FIELD SYSTEM FOR DECONTAMINATION OF BIOLOGICAL AGENTS ON A DIELECTRIC SHEET MATERIAL

FIELD OF THE INVENTION

The present invention relates the field of decontamination of biological agents, and more particularly to a pulsed electric field system for inactivation of biological agents on a dielectric sheet material.

BACKGROUND OF THE INVENTION

High intensity pulsed electric field (PEF) processing is known as an effective means for treating liquid foodstuffs (e.g., water, milk, wine, cognac, water-diluted apple puree, fruit juices, etc.) to inactivate biocontamination, such as microbes, spores, and other biological agents. It has been observed that effective inactivation of biocontaminants in liquid foodstuffs occurs at electric field intensities exceeding 20 kV/cm and temperatures exceeding 40° C. Conventional PEF processing systems include a pulsed high voltage generator and electrodes for forming an electric field in a treatment chamber. The liquid foodstuffs are passed through the electric field to treat the foodstuffs.

Recently, there has been a growing concern over the use by terrorists of biological agents (e.g., anthrax) to contaminate mail, paper currency, and other sheet materials comprised of one or more dielectric materials. Prior art PEF processing systems for treating liquid foodstuffs are not suitable for treating the surfaces of such sheet materials.

The present invention provides a PEF processing system for inactivation of biological agents on the surface of a dielectric sheet material.

SUMMARY OF THE INVENTION

In accordance with the present invention, there is provided a pulsed electric field processing system for treating a dielectric sheet material, comprising: (a) a pulsed voltage generator for generating a pulsed voltage with positive polarity; (b) a first electrode receiving the pulsed voltage of the pulsed voltage generator; (c) a second electrode connected to ground; (d) a dielectric plate arranged between the active electrode and the ground electrode, wherein the dielectric plate and the active electrode are spaced apart to provide a gap between the dielectric plate and the active electrode for receiving the dielectric sheet material, said dielectric plate having a uniform surface profile; and (e) at least one transport assembly for transporting the dielectric sheet material through the gap, wherein the dielectric sheet material is exposed to a pulsed electric field in the gap.

In accordance with another aspect of the present invention, there is provided a method for treating a dielectric sheet material with a pulsed electric field, comprising the steps of: (a) arranging a dielectric plate between an active electrode and a ground electrode, wherein said dielectric plate has a uniform surface profile; (b) transporting the dielectric sheet material through a gap between the dielectric plate and the active electrode; (c) generating a pulsed voltage to produce a pulsed electric field in the gap; and (d) exposing the dielectric sheet material to the pulsed electric field in the gap.

An advantage of the present invention is the provision of a PEF processing system suitable for transporting sheet materials through a pulsed electric field.

Another advantage of the present invention is the provision of a PEF processing system having an electric field generation system that generates relatively low voltage pulses, that produce a pulsed electric field to inactivate biocontamination on surfaces.

A still further advantage of the present invention is the provision of a PEF processing system that activates and deactivates the generation of a pulsed voltage, in accordance with the position of a sheet material in the PEF processing system.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 1 is a schematic diagram of a PEF processing system according to a preferred embodiment of the present invention;

FIG. 2 is cross-sectional view of a portion of the PEF processing system of FIG. 1, taken along line 2—2;

FIG. 3 is a magnified view of the upper surface of a dielectric plate of the PEF processing system, according to a preferred embodiment;

FIG. 4 is a magnified view of the upper surface of a dielectric plate of the PEF processing system, according to an alternative embodiment;

FIG. 5 is a magnified view of the upper surface of a dielectric plate before formation of a uniform surface profile;

FIG. 6 are timing diagrams illustrating the timing associated with activation and deactivation periods of an electric field generation system of the PEF processing system;

FIG. 7 is a graph showing the dependence of electric field strength, in an air gap between a dielectric plate and an active electrode, on the dielectric constant of the dielectric plate; and FIG. 8 is a scanning electron microscopy (SEM) image of the upper surface of a ceramic dielectric plate having a uniform surface profile produced by a water jet treatment process.

DETAILED DESCRIPTION OF A PREFERRED EMBODIMENT

Referring now to the drawings wherein the showings are for the purposes of illustrating a preferred embodiment of the invention only and not for purposes of limiting same, FIG. 1 shows a PEF processing system 10 according to a preferred embodiment of the present invention. PEF processing system 10 is generally comprised of transport assemblies 20 and 30 and an electric field generation system 50. Transport assemblies 20, 30 convey a sheet material through a pulsed electric field generated by electric field generation system 50.

Transport assembly 20 includes rollers 26, and upper and lower conveyer belts 22, 24. Rollers 26 are driven by a motor (not shown), to rotate conveyer belts 22, 24, in a manner well known to those skilled in the art. A gap 28 between conveyer belts 22, 24 is dimensioned to receive a sheet material for conveyance therethrough.

Likewise, transport assembly 30 includes rollers 36, and upper and lower conveyer belts 32, 34. Rollers 36 are driven by a motor (not shown), to rotate conveyer belts 32, 34, in a manner well known to those skilled in the art. A gap 38 between conveyer belts 22, 24 is dimensioned to receive a sheet material 2. As used herein "sheet material" shall refer to paper, currency, postcards, envelopes, thin packages, plastic sheets, and other generally planar materials.

It should be appreciated that transport assemblies 20 and 30 of FIG. 1 are illustrated as shown for the sole purpose of describing a preferred embodiment of the present invention, and are not intended to limit the same. In this regard, transport assemblies 20 and 30 may take any suitable form for conveying sheet material 2 through electric field generation system 50. Gaps 28 and 38 are aligned to define a path "P" through electric field generation system 50.

Electric field generation system 50 is generally comprised of an active electrode 52, a ground electrode 62, a dielectric plate 70, a pulsed voltage generator 90, and a control unit 100.

Pulsed voltage generator 90 includes a pulse generating circuit (not shown) for producing at least one of: exponentially decaying, square wave, bipolar, or oscillatory pulses. Pulse generating circuits are well known to those skilled in the art. For example, a typical pulse generating circuit for producing exponentially decaying pulses is comprised of a DC power supply, a charging resistor, a capacitor bank, including at least one capacitor, and a discharge switch. The DC power supply charges the capacitor bank. When a trigger signal is applied to the discharge switch, the charge stored in the capacitor bank is applied to the electrodes. A typical pulse generating circuit for producing square pulses is comprised of a DC power supply, a charging resistor, a pulse forming network including an array of capacitors and inductors, and a solid state switching device. The frequency of the pulses is typically in the range of 1 to 10,000 Hz, and preferably about 300 to 1000 Hz. The pulses typically have a width in the range of 100 nanoseconds to 100 μsec. In a preferred embodiment, only positive polarity pulses are applied to the electrodes, since negative polarity pulses will electrically discharge in air.

Figure 2:
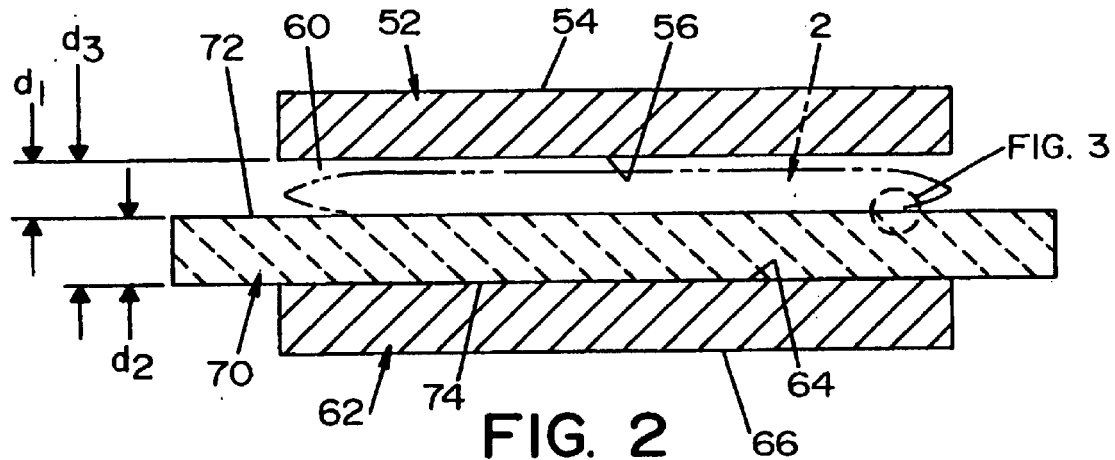

Pulse voltage generator 90 is connected to active electrode 52 and ground electrode 62. As best seen in FIG. 2, active electrode 52 is generally planar, and has an upper surface 54 and a lower surface 56. Ground electrode 62 is generally planar, and has an upper surface 64 and a lower surface 66. Ground electrode 62 is electrically grounded. Electrodes 52 and 62 are spaced apart to provide a gap having a predetermined spacing "$d_3$" (see FIG. 2). Spacing $d_3$ is dimensioned to receive dielectric plate 70 and sheet material 2, as will be described below. Electrodes 52, 62 are made of an electrically conductive material, including, but not limited to stainless steel, tungsten, and the like.

Dielectric plate 70 is generally planar, and has an upper surface 72 and a lower surface 74, as best seen in FIG. 2. Dielectric plate 70 is made of a dielectric material, including, but not limited to, a ceramic, a polymer, a cellulosic (e.g., cellulose acetate), and the like. Dielectric plate 70 is located within spacing $d_3$. In a preferred embodiment, lower surface 74 of dielectric plate 70 is supported by upper surface 64 of ground electrode 62.

Dielectric plate 70 has a thickness "$d_2$," wherein upper surface 72 of dielectric plate 70 is spaced apart from lower surface of active electrode 52 to provide a gap 60 having a spacing of "$d_1$." Gap 60 is dimensioned to allow a sheet material 2 to pass therethrough. Pulsed voltage generator 90 produces a pulsed electric field in gap 60, that is used to treat sheet material 2, as will be described in further detail below.

Control unit 100 provides control signals to pulse generator 90 for activating and deactivating pulse voltage generator 90. When pulse voltage generator 90 is activated it generates a continuous series of pulses. No pulses are generated when pulse voltage generator 90 is deactivated. Control unit 100 preferably takes the form of a microcontroller or personal computer (PC). In an alternative embodiment, control unit 100 may also be programmed to provide control signals to the motors driving rollers 26 and 36. In this manner, control unit 100 may control the travel speed of object 2 through the pulsed electric field.

Sensors 102 and 104 are disposed along path P to provide signals to control unit 100 indicative of the location of sheet material 2 along path P. In this regard, sensors 102 and 104 provide trigger signals respectively indicative of a leading edge 4 and a trailing edge 6 of object 2, as will be described in greater detail below. Sensors 102, 104 preferably take the form of optical sensors, such as photodiodes and the like.

Figure 3:
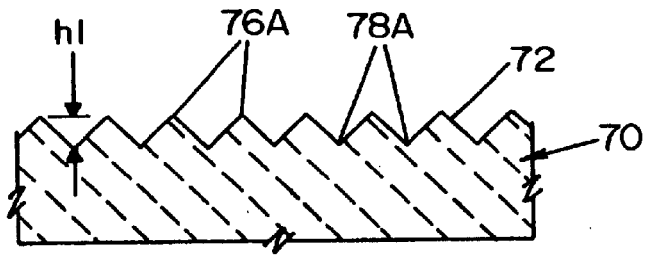
Figure 4:
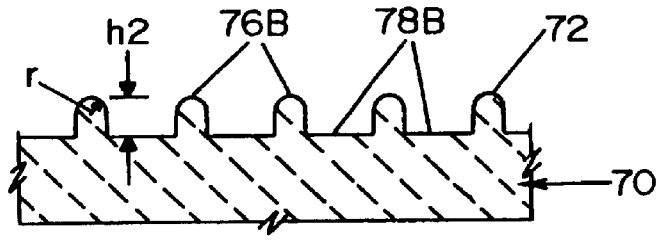

Dielectric plate 70 increases the electric field produced in gap 60 when upper surface 72 of dielectric plate 70 is formed to have a uniform surface profile. As used herein, the term "uniform surface profile" refers to a surface with regularly spaced peaks and valleys, such as shown in the embodiments of FIGS. 3 and 4. The uniform surface profile can be produced using a variety of processes, including but not limited to, a water jet treatment process, an ion etching process, and a laser ablation process. Dielectric plate 70 of FIG. 3 has peaks 76A and valleys 78A, produced by a water jet treatment process. In FIG. 4, peaks 76B and valleys 78B are produced by an ion etching process. Ion etching is a well known method for patterning. In this method, ions are used to bombard the surface of dielectric plate 70, and etch unmasked, exposed areas. The distance h1 from peak 76A to valley 78A (FIG. 3), and distance h2 from peak 76B to valley 78B (FIG. 4) is preferably in the range of 1 to 20 microns. With reference to FIG. 4, the radius r of peak 76B is preferably in the range of 1 to 5 microns.

Figure 5:
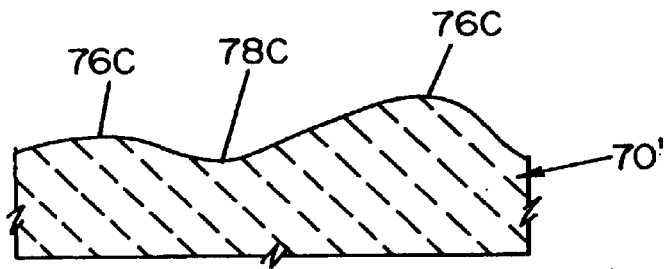

It should be appreciated that a typical prior art dielectric plate 70' (FIG. 5) has an irregular surface with non-uniform peaks 76C and valleys 78C. In contrast, peaks 76A and 76B have a generally uniform height, while valleys 78A and 78B have a generally uniform depth.

Figure 8:
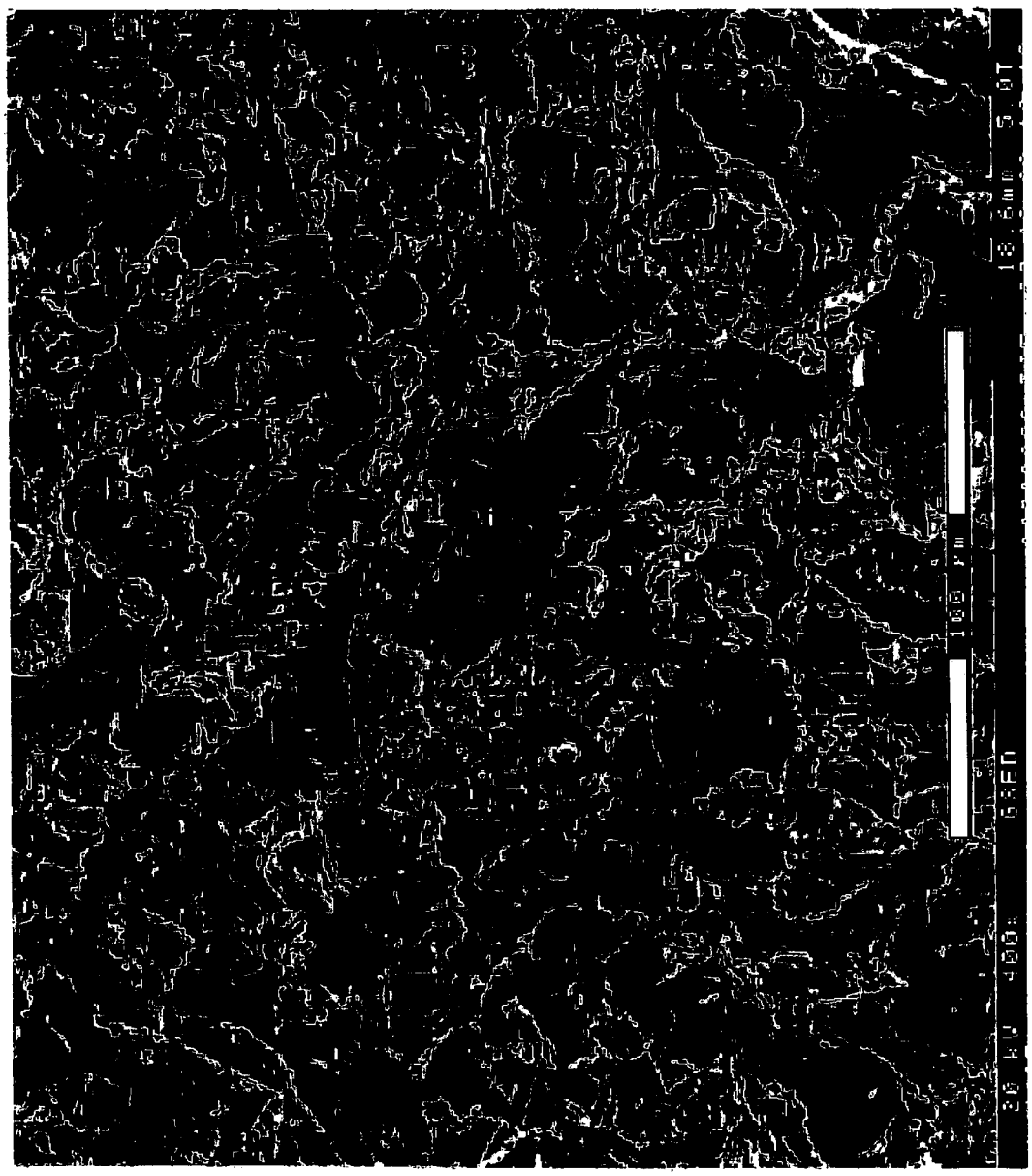

FIG. 8 shows a scanning electron microscopy (SEM) image of the upper surface of a ceramic dielectric plate having a uniform surface profile produced by a water jet treatment process.

Figure 6:
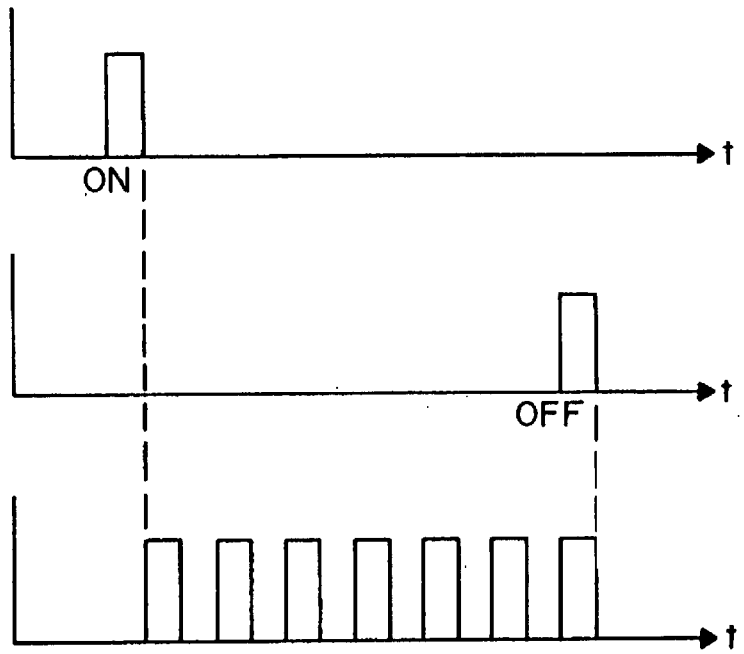

Operation of PEF processing system 10 will now be described in detail with particular reference to FIGS. 1 and 6. A sheet material 2 is loaded into transport assembly 20, and transported through gap 60. When leading edge 4 of sheet material 2 passes sensor 102, sensor 102 communicates an "ON" pulse to control unit 100 (see first timing diagram of FIG. 6). In response to receipt of the ON pulse, control unit 100 activates pulse voltage generator 90 (see second and third timing diagrams of FIG. 6). The pulses generated by pulse voltage generator 90 produce a pulsed electric field within gap 60. Consequently, sheet material 2 is exposed to a pulsed electric field as it travels through gap 60.

The uniform surface profile of dielectric plate 70 provides an increased electric field intensity, as compared with a dielectric plate having a non-uniform surface profile, for the same pulsed voltage level. It should be understood that charge accumulates at the peaks of upper surface 72.

Accordingly, the electric field strength is greatest at the peaks of upper surface 72.

Suitable bioelectric parameters for a PEF system for decontamination of dielectric sheet materials include an electric field strength in the range of 10 to 800 kV/cm, and a pulse duration in the range of 100 nsec to 1 μsec.

The electric field strength (or intensity) E in gap 60 between dielectric plate 70 and active electrode 52 can be determined by the following equation:

$$E = [(V)(\epsilon)]/[d_2 + \epsilon d_1],$$

where:
V is the voltage of each pulse generated by pulse voltage generator 90,
$\epsilon$ will be taken as the permittivity of dielectric plate 70,
$d_1$ is the size of "air" gap 60 (see FIG. 2), and
$d_2$ is the thickness of dielectric plate 70 (see FIG. 2).

Figure 7:
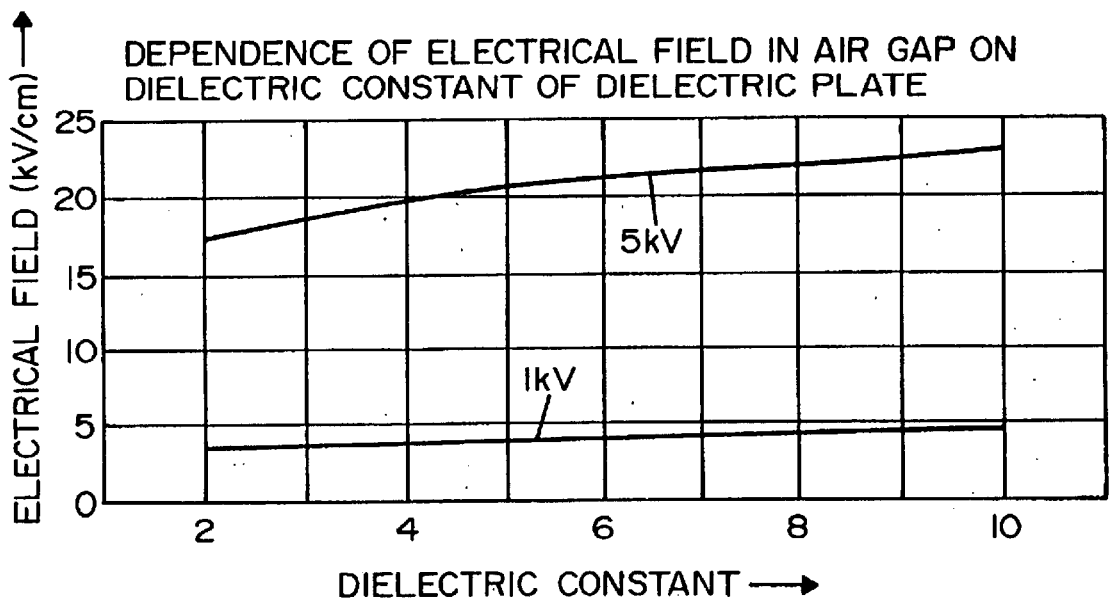

FIG. 7 illustrates the relationship between the electric field strength for air gap size $d_1 = 2$ mm, and the dielectric constant $\kappa$ (where permittivity $\epsilon = \kappa \epsilon_0$), for pulsed voltages V of 1 kV and 5 kV. The dielectric plate has a uniform upper surface, and a thickness $d_2 = 2$ mm.

The average energy of electric field W in air gap 60 can be determined by the following equation:

$$W_{average} = (\tfrac{1}{2}) \epsilon E^2 v$$

where:
$\epsilon$ is the permittivity of free space ($\epsilon_0$), since gap 60 is filled with air,
E is the electric field strength, as determined above, and
v is the volume of space between upper surface 72 of dielectric plate 70 and lower surface 56 of active electrode 52.

Thus, for $\epsilon = \epsilon_0 = 8.85 \times 10^{-12}$ c$^2$/N·m$^2$, E = 20 kV/cm = $20 \times 10^5$ V/m = $20 \times 10^5$ N/C, and v = 1 cm$^3$ = $1 \times 10^{-6}$ m$^3$, $$\begin{aligned}
W_{average} &= \left(\tfrac{1}{2}\right) \varepsilon_0 E^2 v \\
&= \tfrac{1}{2}(8.85 \times 10^{-12} \text{ C}^2/\text{N·m}^2)(20 \times 10^5 \text{ N/C})^2 (1 \times 10^{-6} \text{ m}^3) \\
&= \tfrac{1}{2}(8.85 \times 10 - 12 \text{ C}^2/\text{N·m}^2)(400 \times 10^{10} \text{ N}^2/\text{C}^2)(1 \times 10^{-6} \text{ m}^3) \\
&= 1.770 \times 10^{-5} \text{ Nm} = 1.770 \times 10^{-5} \text{ Joules}
\end{aligned}$$

The energy for each pulse ($W_{pulse}$) can be determined by the following equation:

$$W_{pulse} = (W_{average})/[(t)(f)]$$

where t = pulse duration, and f = pulse frequency. Thus, for t = 100 nsec and f = 300 Hz, $$W_{pulse} = (1.770 \times 10^{-5} \text{ Joules})/[(100 \times 10^{-9} \text{ sec})(300 \text{ Hz})] = 0.60 \text{ Joules}$$
(per pulse)

Absorbed dose D can be determined by the equation:

$$D = W_{pulse}/m$$

where:
$W_{pulse}$ is the energy of the electric field in the gap (per pulse), and
m is the mass of the object being treated in the gap by the electric field.
Thus, for $W_{pulse} = 0.60$ Joules (per pulse) and m = 10 g = $10 \times 10^{-3}$ kg, $$\begin{aligned}
D &= W_{pulse}/m = (0.60 \text{ Joules})/(10 \times 10^{-3} \text{ kg}) \\
&= 60 \text{ J/kg} = 60 \text{ Grays} = 0.060 \text{ kGy}
\end{aligned}$$

In view of the foregoing, 1000 pulses is sufficient to receive an absorbed dose D of 60 kGy. For a frequency f = 1000 Hz, the treatment time is 1 sec. For a frequency of f = 300 Hz, treatment time is 3.33 sec.

It should be appreciated that to effectively inactivate a biocontaminant, absorbed dose D is preferably in the range of 1 to 60 kGy, and more preferably about 60 kGy to inactivate anthrax. As indicated above, pulsed voltage generator 90 has a pulse rate in the range of 1 to 10,000 Hz, and preferably about 300 Hz, to obtain the desired dosing.

Returning now to operation of PEF processing system 10, after leading edge 4 of sheet material 2 passes through gap 60, it is received by transport assembly 30. When trailing edge 6 of sheet material 2 passes sensor 104, sensor 104 communicates an "OFF" pulse to control unit 100 (see second timing diagram of FIG. 6). In response to receipt of the OFF pulse, control unit 100 deactivates pulse voltage generator 90. The timing relationship of the ON pulse, the OFF pulse, and the pulses generated by pulse voltage generator 90 is shown in FIG. 6. It should be appreciated that the travel speed of sheet material 2 through the pulsed electric field in gap 60 is determined by the speed of the motors of transport assemblies 20 and 30. As indicated above, control unit 100 may be programmed to provide control signals to the motors driving rollers 26 and 36, thus controlling the travel speed of object 2 through the pulsed electric field.

Other modifications and alterations will occur to others upon their reading and understanding of the specification. It is intended that all such modifications and alterations be included insofar as they come within the scope of the invention as claimed or the equivalents thereof.

What is claimed is:

1. A pulsed electric field processing system for treating a dielectric sheet material, comprising:
    a pulsed voltage generator for generating a pulsed voltage with positive polarity;
    control means to provide control signals to said pulsed voltage generator for activation and deactivation thereof;
    first sensing means for sensing a leading edge of said dielectric sheet material; and
    second sensing means for sensing a trailing edge of said dielectric sheet material,
    wherein said control means activates said pulsed voltage generator in response to the first sensing means sensing the leading edge, and deactivates said pulsed voltage generator in response to the second sensing means sensing the trailing edge;
    a first electrode receiving the pulsed voltage of the pulsed voltage generator;
    a second electrode connected to ground;
    a single dielectric plate arranged between the first electrode and the second electrode, wherein the dielectric plate and the first electrode are spaced apart to provide an open gap between a surface of the dielectric plate and a surface of the first electrode for receiving the dielectric sheet material, said dielectric plate having a uniform surface profile; and
    at least one transport assembly for transporting the dielectric sheet material through the gap, wherein the dielectric sheet material is exposed to a pulsed electric field in the gap.

2. A pulsed electric field processing system as defined by claim 1, wherein said uniform surface profile of said dielectric plate includes a plurality of peaks and valleys.

3. A pulsed electric field processing system as defined by claim 1, wherein said pulsed voltage generator includes a pulse generating circuit for producing at least one of: exponentially decaying, square wave, bipolar, and oscillatory pulses.

4. A pulsed electric field processing system as defined by claim 1, wherein said dielectric plate is comprised of a material selected from the group consisting of: a ceramic, a polymer, and a cellulosic.

5. A pulsed electric field processing system as defined by claim 1, wherein the uniform surface profile of said dielectric plate is formed by a process selected from the group consisting of: water jet treatment, ion etching and laser ablation.

* * * * *